(12) United States Patent
Datar et al.

(10) Patent No.: US 12,299,882 B2
(45) Date of Patent: May 13, 2025

(54) METHOD FOR DETECTION AND CHARACTERIZATION OF LESIONS

(71) Applicant: Siemens Healthcare GmbH, Erlangen (DE)

(72) Inventors: Manasi Datar, Erfurt (DE); Arnaud Arindra Adiyoso, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 256 days.

(21) Appl. No.: 17/954,922

(22) Filed: Sep. 28, 2022

(65) Prior Publication Data

US 2024/0104722 A1 Mar. 28, 2024

(51) Int. Cl.
*G06T 7/00* (2017.01)
*A61B 6/00* (2024.01)
*G06V 10/44* (2022.01)

(52) U.S. Cl.
CPC .......... *G06T 7/0012* (2013.01); *A61B 6/5217* (2013.01); *G06V 10/443* (2022.01); *G06T 2207/20084* (2013.01); *G06T 2207/30096* (2013.01)

(58) Field of Classification Search
None
See application file for complete search history.

(56) References Cited

U.S. PATENT DOCUMENTS

| 11,244,191 | B2* | 2/2022 | Yao | G06F 18/214 |
| 11,270,447 | B2* | 3/2022 | Liu | G06T 7/11 |
| 2022/0058805 | A1* | 2/2022 | Lee | G06F 18/24 |
| 2023/0154141 | A1* | 5/2023 | Yu | G06V 10/454 |
| | | | | 706/25 |
| 2023/0410296 | A1* | 12/2023 | Xia | G06T 7/0012 |

OTHER PUBLICATIONS

Dou, Tianyou, Lijuan Zhang, and Wu Zhou. "3d deep feature fusion in contrast-enhanced mr for malignancy characterization of hepatocellular carcinoma." 2018 IEEE 15th International Symposium on Biomedical Imaging (ISBI 2018) IEEE (Year: 2018).*
Lee, Sang-Gil, et al. "Robust end-to-end focal liver lesion detection using unregistered multiphase computed tomography images." IEEE Transactions on Emerging Topics in Computational Intelligence 7.2, pp. 319-329 (Year: 2021).*
Turco, Simona, et al. "Interpretable machine learning for characterization of focal liver lesions by contrast-enhanced ultrasound." IEEE transactions on ultrasonics, ferroelectrics, and frequency control 69, No. 5, pp. 1670-1681 (Year: 2022).*
(Continued)

*Primary Examiner* — Scott A Rogers
(74) *Attorney, Agent, or Firm* — Harness, Dickey & Pierce, P.L.C.

(57) ABSTRACT

A method for detection and characterization of lesions includes acquiring a plurality of phase images of a multiphase imaging exam, extracting a local context for each phase image of the plurality of phase images, encoding the local contexts to create phase specific feature maps, combining the phase-specific feature maps to create unified feature maps, and at least one of characterizing or detecting a lesion based on the unified feature maps.

18 Claims, 8 Drawing Sheets

(56) References Cited

OTHER PUBLICATIONS

Xu, Xingxin, et al. "A knowledge-guided framework for fine-grained classification of liver lesions based on multi-phase CT images." IEEE Journal of Biomedical and Health Informatics 27, No. 1, pp. 386-396 (Year: 2022).*

Sun, Changjian, et al. "Automatic segmentation of liver tumors from multiphase contrast-enhanced CT images based on FCNs." Artificial intelligence in medicine 83, pp. 58-66 (Year: 2017).*

Coenegrachts K. et al.:"Magnetic resonance imaging of the liver: New imaging strategies for evaluating focal liver lesions" World J Radiol, Bd. 1, Nr. 1, p. 72-85, 2009.

Tian Z et al.:"FCOS: Fully Convolutional One-Stage Object Detection," in ICCV, 2019, arXiv:1904.01355v5 [cs.CV] Aug. 20, 2019.

Zhou X. et al.:"Objects as Points," arXiv:1904.07850, 2019.

Ronneberger et al.: "U-Net: Convolutional Networks for Biomedical Image Segmentation"; Medical Image Computing and Computer-Assisted Intervention—MICCAI 2015 : 18th International Conference, Munich, Germany, Oct. 5-9, 2015; Oct. 9, 2015.

Hosny A., et.al., "Artificial intelligence in radiology," Nat Rev Cancer (2018).

Delgado A.F. et al.:"Diagnostic value of alternative techniques to gadolinium-based contrast agents in MR neuroimaging—a comprehensive overview". (2019) 10:84 https://doi.org/10.1186/s13244-019-0771-1.

Zhou J. Wang W. et al.:"Automatic Detection and Classification of Focal Liver Lesions Based on Deep Convolutional Neural Networks: A Preliminary Study," Front. Oncol. (2021).

Lee E.K. et al.:"Importance of Contrast-Enhanced Fluid-Attenuated Inversion Recovery Magnetic Resonance Imaging in Various Intracranial Pathologic Conditions," Korean J Radiol, Bd. 17, Nr. 1, p. 127-141, 2016.

Ozdemir O. et al.:"A 3D Probabilistic Deep Learning System for Detection and Diagnosis of Lung Cancer Using Low-Dose CT Scans," IEEE Trans Med Imaging (2019).

Huang G. et al.:"Densely Connected Convolutional Networks," in CVPR, 2017.

Smirniotopoulus J.G. et al.:"Patterns of Contrast Enhancement in the Brain and Meninges," RadioGraphics, Bd. 27, p. 525-551, 2007.

He, Kaiming, et al. "Deep Residual Learning for Image Recognition" Proceedings of the IEEE Conference on Computer Vision and Pattern Recognition, pp. 770-778, 2016; 2016.

Yasaka K. et al.:"Liver Fibrosis: Deep Convolutional Neural Network for Staging by Using Gadoxetic Acid-enhanced Hepatobiliary Phase MR Images" Radiology, Bd. 287, Nr. 1, pp. 146-155, 2018.

Yasaka K. et al.:"Deep Learning with Convolutional Neural Network for Differentiation of Liver Masses at Dynamic Contrast-enhanced CT: A Preliminary Study," Radiology, Bd. 286, Nr. 3, pp. 887-896, 2018.

* cited by examiner

MRI

METHOD FOR DETECTION AND CHARACTERIZATION OF LESIONS

TECHNICAL FIELD

One or more example embodiments relate to characterization of lesions using a dynamic enhancement pattern in multi-phase imaging. One or more example embodiments additionally relate to an evaluation device, a computer program and an electronically readable data medium.

BACKGROUND

Detection and characterization of lesions in multi-phase imaging are challenging and involve examining corresponding regions across different phases to localize and characterize each instance. In current clinical practice, such evaluation is mainly performed by radiologists manually and the results are generally influenced by their experience and are therefore subjective. Furthermore, the high workload of radiologists may lead to errors and increased uncertainty.

Various deep learning (DL) methods have been applied for lesion detection and characterization in imaging data. These include methods that work on single phase images or in a phase-agnostic manner for multi-phase data. High variability in lesion appearance between phases makes it difficult to converge during training. Another set of methods performs detection and characterization on individual phases before combining the results into the final output. The performance of such methods is affected in settings where phase acquisition is not standardized due to variability in the clinical protocol. 3D models have also been explored to take advantage of the volumetric context and detailed structural information present in volumetric scans. However, these may become intractable due to the large number of parameters leading to slow convergence during training or slow inference speed.

SUMMARY

Studies have shown that dynamic enhancement patterns differ based on lesion type and the type of multi-phase imaging. Therefore, knowledge of the patterns and mechanisms of lesion enhancement is crucial to improving the performance of lesion detection and characterization. It should be noted that existing methods discussed above ignore the dynamic enhancement patterns of specific lesions in the presence of multi-phase imaging.

At least one example embodiment provides a deep learning method for learning and utilizing an enhancement pattern via multi-phase feature fusion followed by combined detection and characterization.

At least one example embodiment provides a method for detection and characterization of lesions, the method including acquiring a plurality of phase images of a multi-phase imaging exam, extracting a local context for each phase image of the plurality of phase images, encoding the local contexts to create phase specific feature maps, combining the phase-specific feature maps to create a unified feature map, and at least one of characterizing or detecting a lesion based on the unified feature map.

According to at least one example embodiment, combining the phase-specific feature maps includes combining the phase-specific feature maps chronologically.

According to at least one example embodiment, combining the phase-specific feature maps includes concatenating the phase-specific feature maps along a channel dimension of the phase-specific feature maps.

According to at least one example embodiment, combining the phase-specific feature maps includes stacking the phase-specific feature maps chronologically across a channel dimension of the phase-specific feature maps.

According to at least one example embodiment, combining the phase-specific feature maps includes linearly combining the phase-specific feature maps.

According to at least one example embodiment, linearly combining the phase-specific feature maps includes combining the phase-specific feature maps using phase-wise weights.

According to at least one example embodiment, extracting the local context includes segmenting the plurality of phase images based on a mask of an organ of interest.

According to at least one example embodiment, extracting the local context includes sequentially extracting sub-images from the plurality of phase images.

According to at least one example embodiment, encoding the local context includes encoding the phase-specific feature maps using a convolutional neural network architecture.

According to at least one example embodiment, the convolutional neural network architecture may be trained via an end-to-end training pipeline.

At least one example embodiment provides a device for detecting and characterizing lesions. The device includes a memory and processing circuitry configured to cause the device to acquire a plurality of phase images of a multi-phase imaging exam, extract a local context for each phase image of the plurality of phase images, encode the local contexts to create phase-specific feature maps, combine the phase-specific feature maps to create a unified feature map, and at least one of characterize or detect a lesion based on the unified feature map.

At least one example embodiment provides a non-transitory computer readable storage medium storing computer executable instructions that, when executed, cause an information processing device to perform a method for detecting and characterizing lesions. The method includes acquiring a plurality of phase images of a multi-phase imaging exam, extracting a local context for each phase image of the plurality of phase images, encoding the local contexts to create phase-specific feature maps, combining the phase-specific feature maps to create a unified feature map, and at least one of characterizing or detecting a lesion based on the unified feature map.

BRIEF DESCRIPTION OF THE DRAWINGS

Other objects and features of the present invention will become apparent from the following detailed description considered in conjunction with the accompanying drawings. The drawings, however, are only examples and schematic solely for the purpose of illustration and do not limit the invention. The drawings show.

FIB. 2B is representative images of FLLs in different phases of a multi-phase dynamic contrast-enhanced computed tomography (CE-CT) exam.

DETAILED DESCRIPTION

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

Detailed illustrative embodiments are disclosed herein. However, specific structural and functional details disclosed herein are merely representative for purposes of describing example embodiments. The example embodiments may, however, be embodied in many alternate forms and should not be construed as limited to only the embodiments set forth herein.

Figure 1A:
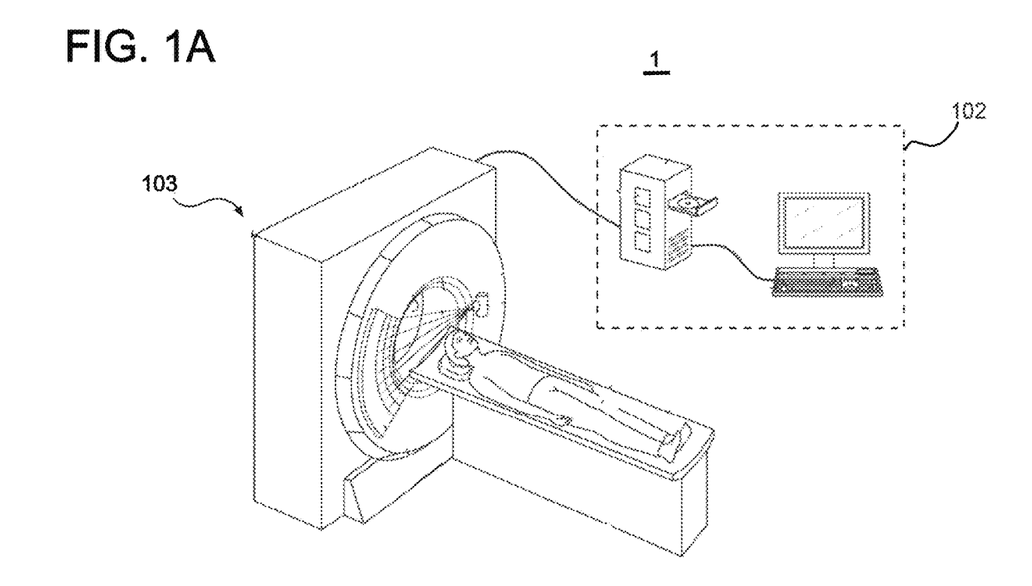
FIG. 1A is an illustration of a system according to example embodiments.

FIG. 1A is an illustration of a system according to example embodiments.

Figure 1B:
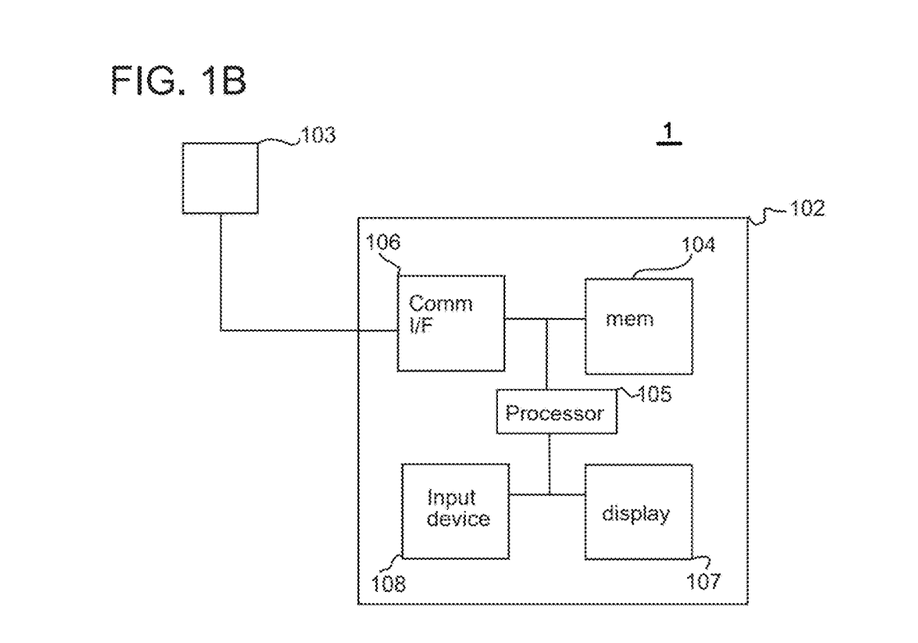
FIG. 1B is a block diagram illustrating an example embodiment of a system according to example embodiments

FIG. 1B is a block diagram illustrating an example embodiment of a system according to example embodiments.

Referring to FIGS. 1A and 1B, a system 1 comprises an information processing device 102 and an acquisition device 103. The information processing device 102 implements a method for processing medical data, especially medical image data. The acquisition device 103 is used to provide medical data to the information processing device 102. In the example the acquisition device 103 is shown as a separate unit from the information processing device 102. It is however possible to integrate the information processing device 102 as part of the acquisition device 103. According to some example embodiments, the acquisition device 103 may be a computer tomograph (CT), however example embodiments are not limited thereto. For example, the acquisition device 103 may be a magnetic resonance imaging (MRI) machine, a positron emission tomography (PET) machine, an ultrasound (US) machine, or an angiography machine. For ease of description, the acquisition device 103 will be described as a CT herein.

The information processing device 102 may include a memory 104, processing circuitry (such as at least one processor 105), a communication interface 106 and/or an input device 108. The memory 104 may include various special purpose program code including computer executable instructions which may cause the information processing device 102 to perform the one or more of the methods of the example embodiments. The acquisition device 103 may provide the medical data to the information processing device 102 via the communication interface 106.

Figure 2A:
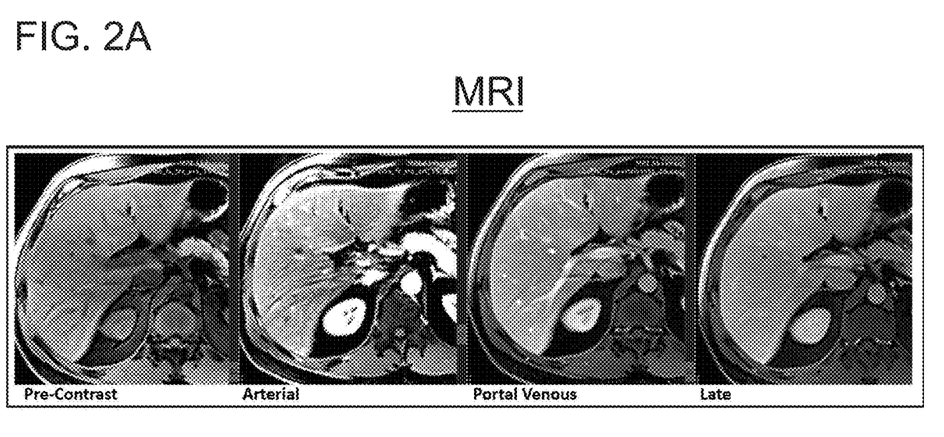
FIG. 2A is representative images of focal liver lesions (FLLs) in different phases of a multi-phase dynamic contrast-enhanced magnetic resonance imaging (CE-MRI) exam.

FIG. 2A is representative images of focal liver lesions (FLLs) in different phases of a multi-phase dynamic contrast-enhanced magnetic resonance imaging (CE-MRI) exam.

Figure 2B:
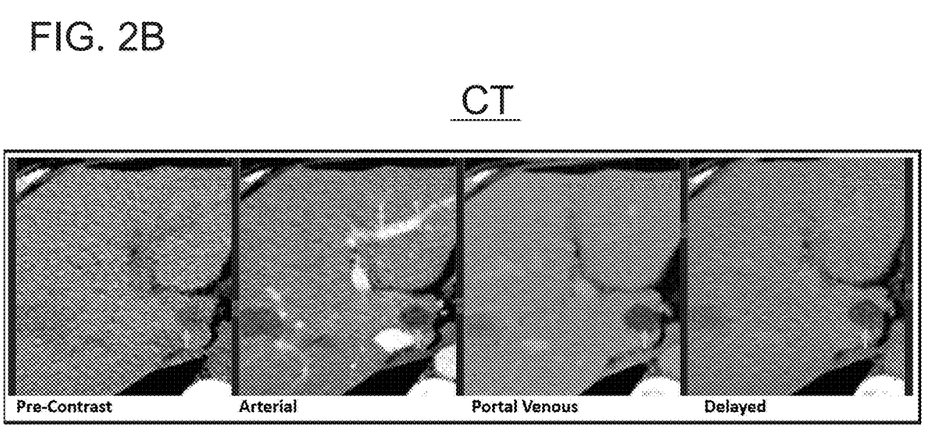

FIG. 2B is representative images of focal liver lesions (FLLs) in different phases of a multi-phase dynamic contrast-enhanced computed tomography (CE-CT) exam.

Referring to FIGS. 2A and 2B, representative examples of focal liver lesions in chronological CE-MRI and CE-CT phases are shown. The CE-CT multi-phase images shown in FIG. 2B represent CT images that may be captured using the acquisition device 103. However, example embodiments are not limited thereto and the multi-phase images may be CE-MRI (as shown, e.g., in FIG. 2A), CE-US, angiography, or PET images. Further, the multi-phase images shown in FIGS. 2A and 2B are of a liver of a patient, however example embodiments are not limited thereto and the images may be of another organ of a patient. Multi-phase imaging (e.g., contrast-enhanced (CE), functional, and/or computational imaging) is commonly used for lesion detection/characterization and plays an important role in the diagnosis, planning, and treatment process. Example applications include cancer staging using CE-CT/MRI, metastasis detection using DWI-MRI, patient monitoring following chemo-/radio-therapy using PET-CT, and diagnosis of blood vessel conditions using CE-US or CT-Angiography.

Each set of example multi-phase images shown in FIGS. 2A and 2B include four images representing four phases: pre-contrast, arterial, portal venous, and late (delayed). However, example embodiments are not limited thereto and the multi-phase images may include images from three phases or images from more than four phases.

Figure 3A:
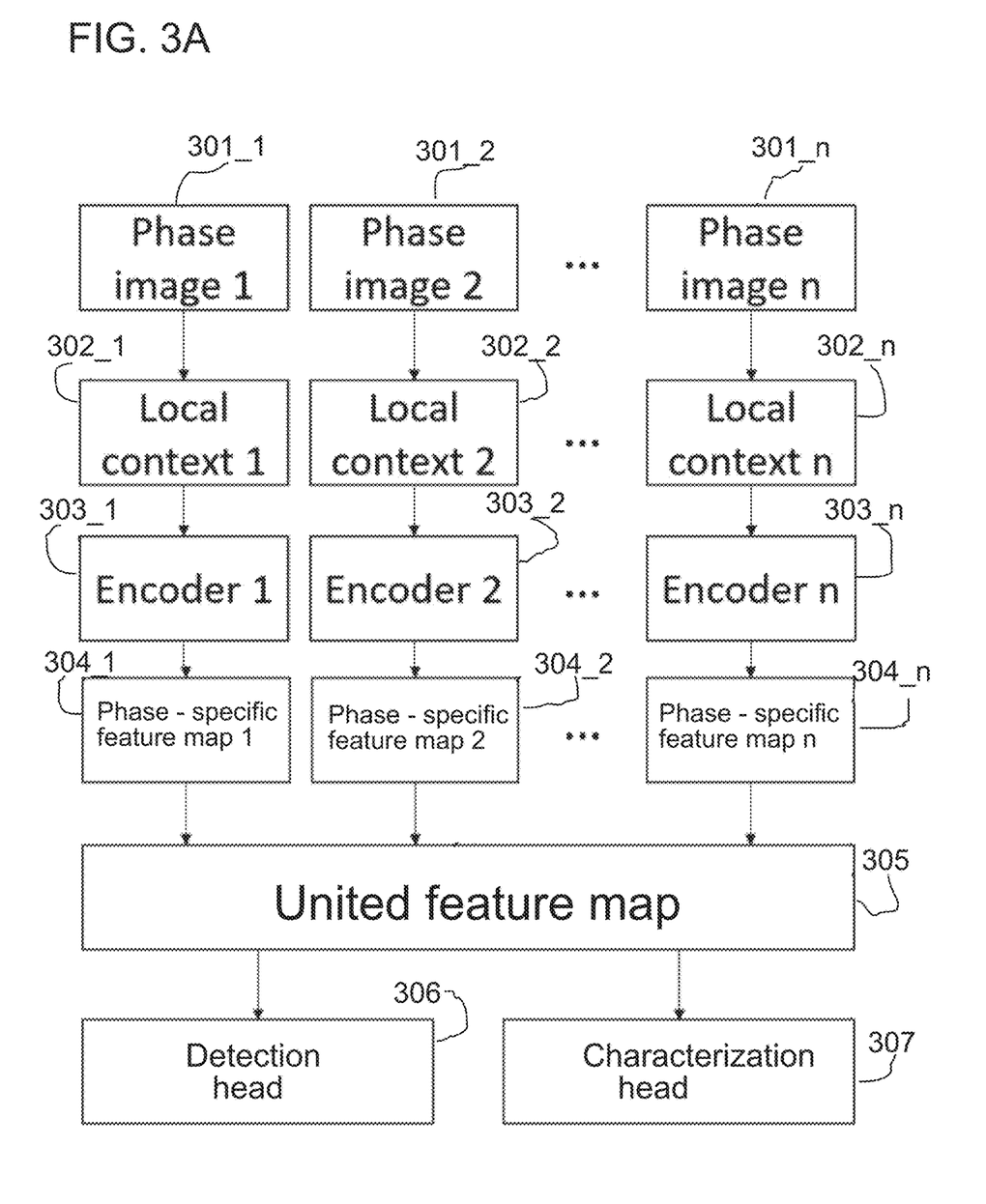
FIG. 3A illustrates a method according to example embodiments.

FIG. 3A illustrates a method according to example embodiments.

Referring to FIG. 3A, the information processing device 102 receives a set of multi-phase images phase image 301_1 to phase image 301_$n$ (collectively, phase images 301), where n is an integer greater than 2. For example, the information processing device 102 may receive the phase images 301 from the acquisition device 103. The phase images 301 may include a set of images for individual phases of a multi-phase imaging exam (e.g., the pre-contrast (unenhanced), arterial, and portal venous phase images in a CE-CT exam as shown in FIG. 2B). However, example embodiments are not limited to the images shown in FIG. 2B and the phase images 301 may include T1-/T2-weighted, DWI, and/or ADC images in case of an MRI/DWI exam.

Further, the phase images 301 may include images for three individual phases or four or more individual phases of a multi-phase imaging exam.

As shown in FIG. 3A, the information processing device 102 may then extract local contexts 302_1-302_n (collectively, local contexts 302) corresponding, respectively, to phase images 301_1-301_n. The local contexts 302 may be extracted for each phase image 301 based on the requirements of the task. For example, for a liver lesion segmentation, liver or abdominal regions of phase images 301_1-301_n may be extracted as the local context 302_1-302_n, respectively. Some example methods for extracting a local context 302 for a phase image 301 will be described later with regard to FIGS. 4A and 4B. The local contexts may be extracted via a local context extractor 610.

As shown in FIG. 3A, the information processing device 102 encodes the local contexts 302_1-302_n into phase-specific feature maps 304_1-304_n (collectively, phase-specific feature maps 304) corresponding, respectively, to local contexts 302_1-302_n. The information processing device 102 may encode the local contexts 302_1-302_n using encoders 303_1-303_n (collectively, encoders 303), respectively. Each encoder 303 may comprise a 2D/3D convolutional neural network (CNN) architecture such as a UNet, a ResNet or a DenseNet. However, example embodiments are not limited thereto, and any known CNN architecture may be used. Each encoder 303 may be trained specifically to perform the particular segmentation/classification task. For example, an encoder 303 used for encoding a feature map of a liver lesion segmentation of a phase 2 phase image may have been specifically trained to encode a feature map from a local context corresponding to a phase 2 phase image. For example, the encoders 303 may be trained via an end-to-end pipeline training method. An end-to-end training method according to example embodiments will be discussed in more detail later with reference to FIGS. 6A and 6B.

Each of the local contexts 302_1-302_n is encoded as a set of C feature maps corresponding to a respective input phase image (e.g., n sets of C feature maps), where C is the number of output channels of the final encoder layer (e.g. for ResNet-50, C=2048) of the corresponding encoder 303. Each set of C feature maps includes a width W and height H. The values W and H depend on the width and height of the original image and the kernel size, stride, and padding parameters used for the various convolution layers in the encoder 303. The dimension C (channels) corresponds to the number of filters in the final convolutional layer in the encoder 303. Each of the C filters results in a feature map of size W×H, leading to the final feature map dimensions of W×H×C of each phase-specific feature map 304_1-304_n corresponding, respectively, to each phase image 301_1-301_n.

The phase-specific feature maps 304 represent higher-level semantic information for each phase. According to example embodiments, the phase-specific feature maps 304_1-304_n may be combined (fused) together into a unified feature map 305 to provide information across underlying image phases. The information across underlying image phases may include information specific to a chronology of the image phases.

As shown in FIG. 3A, the information processing device 102 combines (fuses) the phase-specific feature maps 304_1-304_n chronologically, based on a chronological order derived from the sequence in which the phase images 301_1-301_n are acquired in a contrast enhanced imaging exam (CE exam), as the unified feature map 305. The information processing device 102 may combine the phase-specific feature maps 304_1-304_n via a feature fusion engine 620. The feature fusion engine 620 may be trained via an end-to-end pipeline training method. An end-to-end training method according to example embodiments will be discussed in more detail later with reference to FIGS. 6A and 6B.

A detailed explanation as to how the information processing device 102 combines the phase-specific feature maps 304_1-304_n will be described later with reference to FIGS. 5A-5C.

Finally, as shown in FIG. 3A, the information processing device 102 localizes (detects) and/or classifies lesions based on the unified feature map 305. The information processing device 102 may use one or more detection head 306 and/or one or more characterization head 307 to localize and/or classify the lesions.

Each, or one or more, of the detection head 306 may be, for example a fully connected layer of a CNN that outputs the corners of the bounding box/cube of the lesion (2D: 4 values, 3D: 8 values), a set of convolutional decoders that outputs a keypoint heatmap, a local offset, and a size of a bounding box/cube of the lesion respectively (e.g., 2D: 5 values, 3D: 7 values), or a convolutional decoder that outputs the lesions as positive regions in a mask. Each of the one or more characterization head 307 may be, for example, a fully connected layer of a CNN that outputs the class/category of the lesion (e.g., benign, or malignant) as a numerical value or a fully connected regression layer of a CNN that outputs a severity score within a known (or given) range (e.g., 0 and 1).

The detection and/or characterization heads 306 and 307 may be implemented similar to anchor-less approaches like the FCOS or Centernet or similar to image-to-image approaches such as the expansion (decoder) branch of the U-net. The FCOS and Centernet algorithms are popularly implemented for detection in 2D images. In case of medical applications requiring detection in 3D volumes, the 2D convolution layers in these architectures is replaced with 3D convolution layers and the output dimensions are modified accordingly as well. The detection and/or characterization heads 306 and 307 may be trained via an end-to-end pipeline training method. An end-to-end training method according to example embodiments will be discussed in more detail later with reference to FIGS. 6A and 6B.

For tasks such as lesion tracking and follow up scans, detection followed by lesion matching according to any known method may be employed.

Figure 3B:
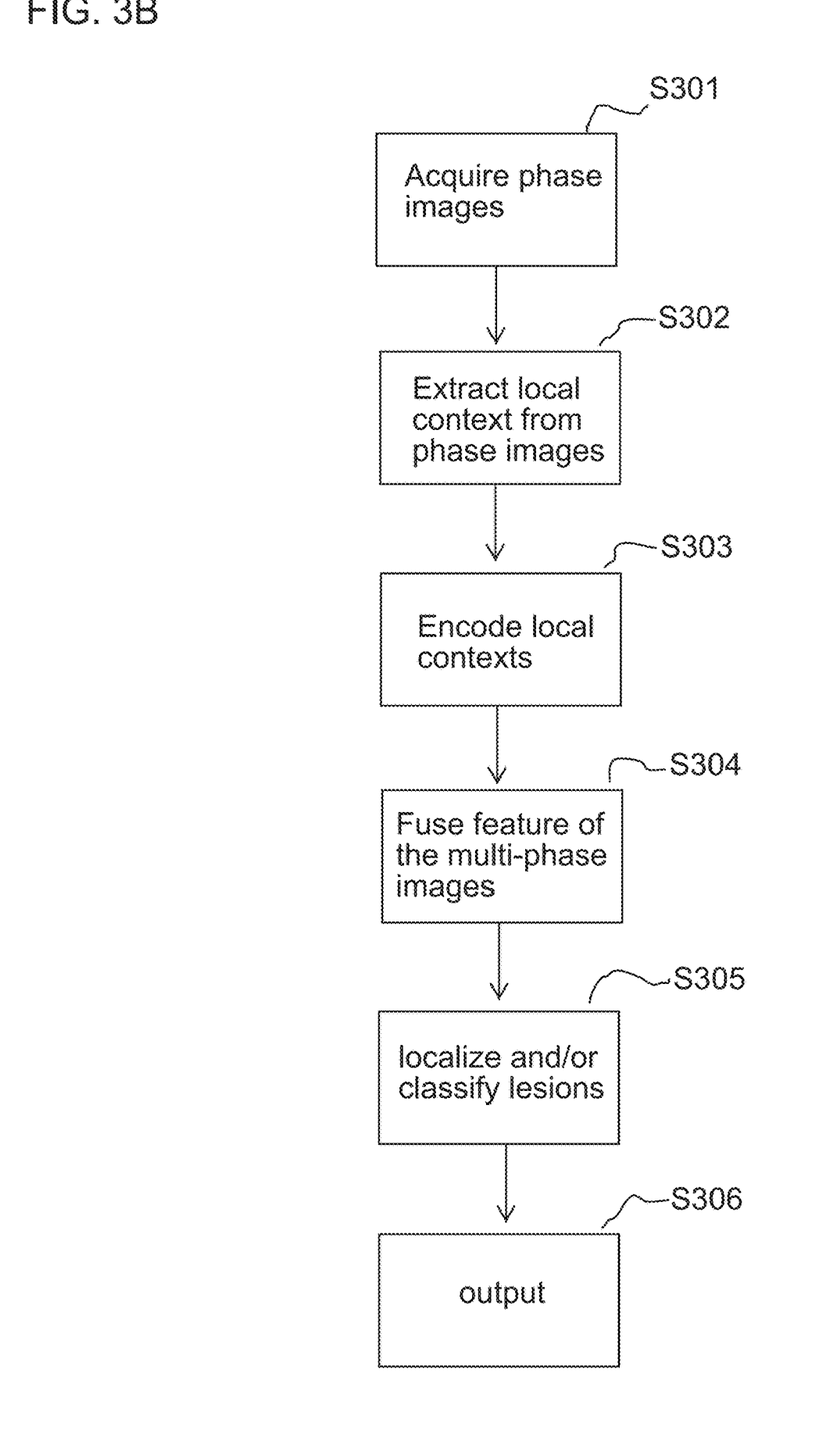
FIG. 3B is a flow chart illustrating a method according to example embodiments.

FIG. 3B is a flow chart illustrating a method according to example embodiments.

The operations shown in FIG. 3B may be similar to those described with reference to FIG. 3A. Repeated description has been omitted for brevity.

Referring to FIG. 3B, at step S301 the information processing device 102 receives a set of multi-phase images, phase image 301_1-301_n.

At step S302, the information processing device 102 extracts a local context, local context 302_1-302_n, for each phase image 301_1-301_n based on the requirements of the task.

At step S303, the information processing device 102 encodes features of the individual phases as phase-specific feature map 304_1-304_n using encoders 303_1-303_n, respectively, based on the local contexts 302_1-302_n, respectively.

At step S304, the information processing device 102 combines (fuses) the phase-specific feature maps 304_1-304_n chronologically as unified feature map 305.

At step S305, the information processing device 102 localizes (detects) and/or classifies lesions, using the at least one detection head 306 and/or the at least one characterization head 307, based on the unified feature map 305.

At step S306, the information processing device 102 outputs the localized and/or classified lesions. For example, the information processing device 102 may display, on the display 107, an image of the organ of the patient with the lesion at least one of highlighted and/or labelled.

Studies have shown that knowledge about dynamic enhancement patterns of specific lesions improves lesion characterization and helps obtain the correct differential diagnosis for staging, therapy, and treatment planning in current clinical practice. The deep learning based detection/characterization method according to the example embodiments leverages such knowledge to improve performance over the current radiology workflow.

The method according to example embodiments combines features from available phases to learn the evolution of a lesion enhancement pattern over the course of the multi-phase scan and therefore may be applicable to all multi-phase exams—contrast enhanced, functional, etc.

By combining (fusing) features of images of the multi-phase examination prior to detecting or characterizing the lesions via the detection/characterization heads, lesion detection and/or characterization by the detection/characterization may be more accurate. Further, the detection/characterization heads do not require an additional merging step and may operate more quickly and/or require less computational effort when run on the unified feature map 305 according to example embodiments.

Different types of lesions show different enhancement patterns over the course of a multi-phase scan. Therefore, specific lesions may only be visible in some phase images based on their particular enhancement characteristics. Thus, features computed from different phases contain complementary information. Combining features via feature fusion, according to example embodiments, may improve detection performance. Maintaining the chronological order while combining features, according to example embodiments, allows the method to learn the enhancement pattern, which is relevant for more accurate lesion characterization.

Lesion appearance may vary between corresponding individual phases of the same multi-phase exam from different clinical settings due to a variability in the underlying clinical protocols. The multi-phase feature fusion according to example embodiments can be tuned to learn the lesion enhancement pattern based on the differences between individual phases rather than the appearance in any individual phase, therefore making it robust in the presence of varying clinical protocols.

An encoder designed according to the example embodiments can also be used as a pre-trained encoder for other applications involving multi-phase exams such as longitudinal tracking of lesions during/after procedures or for follow-up.

Figure 4A:
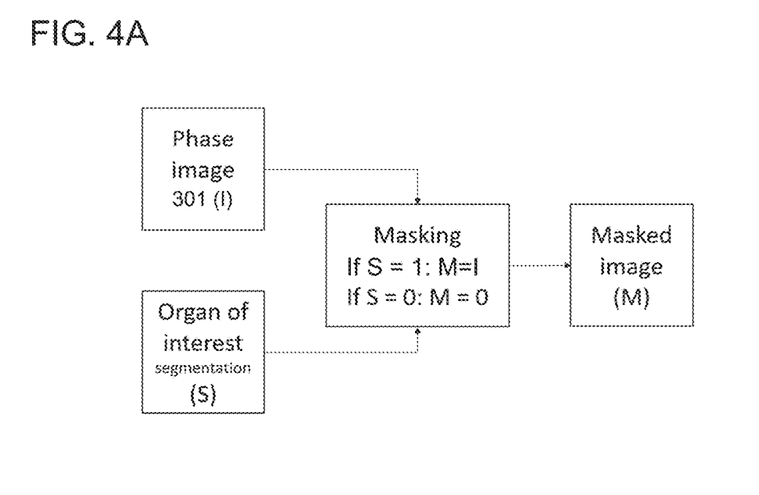
FIG. 4A illustrates an example method for extracting a local context from a phase image according to example embodiments

FIG. 4A illustrates an example method for extracting a local context from a phase image according to example embodiments.

Referring to FIG. 4A, a method for extracting a local context from a phase image 301 using available (binary) segmentation S of an organ of interest is shown. For tasks specific to a given organ of interest (e.g., segmentation of focal liver lesions), a segmentation of the organ (e.g., binary mask S of the liver) may be used to extract the local context. Such a mask S may be obtained from a separate segmentation algorithm, or a delineation drawn by an expert. Only the image values underneath the mask are used while the values outside the mask are set to 0, as shown in FIG. 4A. The region outside the mask may further be cropped out of the local context. Restated, as shown in FIG. 4A, an input phase image 301 (I) may be processed based on an available binary segmentation (S) to produce a masked output (M), which can be used as the local context 302.

Figure 4B:
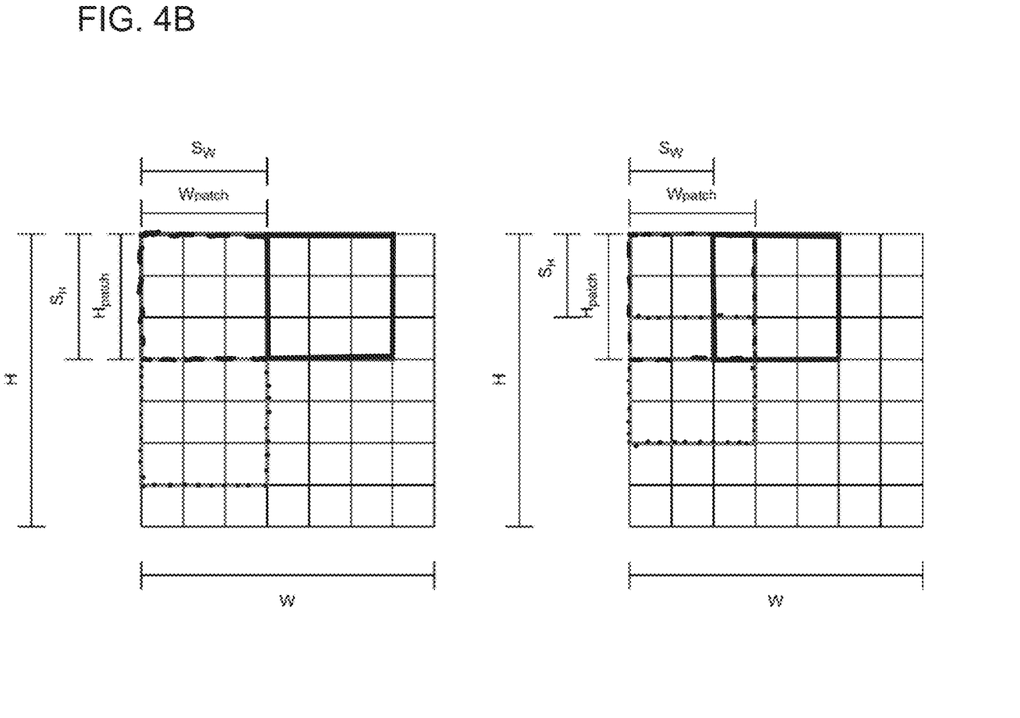
FIG. 4B illustrates another example method for extracting a local context from a phase image according to example embodiments.

FIG. 4B illustrates another example method for extracting a local context 302 from a phase image 301 according to example embodiments.

Referring to FIG. 4B, a method for extracting a local context 302 by sampling sub-images is shown. In patch-based approaches, a series of sub-images (patches) of a pre-defined size can be used as the local context 302. These sub-images (patches) can be extracted sequentially from an input phase image 301 with or without overlap, as shown in FIG. 4B. The size of the patch is $H_{patch} \times W_{patch}$, where $H_{patch} < H$ and $W_{patch} < W$. Patches are sampled with stride of $s_H$ and $s_W$. The sampling is performed without overlap if $s_H = H_{patch}$ and $s_W = W_{patch}$, and with overlap if $s_H < H_{patch}$ or $s_W < W_{patch}$. This approach is also known as tiling and uses information from the entire image.

Task-relevant prior knowledge or other statistical methods may also be used to influence the sampling strategy and use sub-images (patches) only from the relevant regions. Such sampling strategies may be combined with segmentation/registration approaches, such as those described above with reference to FIG. 4A.

Example embodiments are understood as not being limited to the example methods for extracting the local context 302 from the phase image 301 illustrated by FIGS. 4A and 4B and described above. Any known method for extracting a local context from an image may be used.

The local context extraction according to example embodiments is not meant to be understood as precluding other preprocessing steps such as image normalization, intensity filtering, registration to align with a common frame of reference, etc. Accordingly, any known preprocessing steps may be performed on the multi-phase images prior to extracting the local context.

Figure 5A:
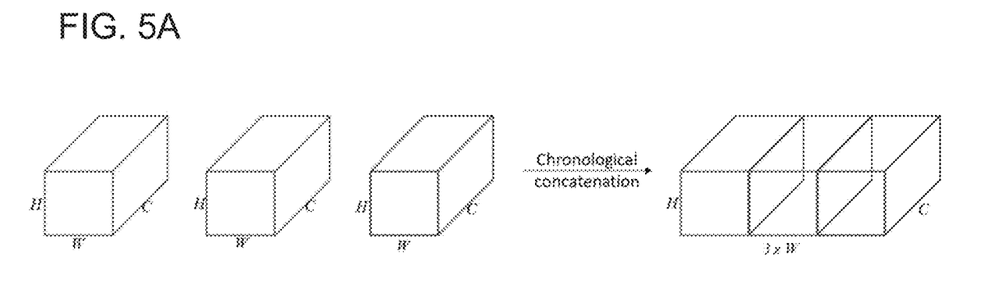
FIG. 5A illustrates an example method for performing feature fusion of feature maps, according to example embodiments.

FIG. 5A illustrates an example method for performing feature fusion of feature maps, according to example embodiments.

Referring to FIG. 5A, the information processing device 102 may combine (fuse) the phase-specific feature maps 304_1-304_n to the unified feature map 305 via a chronological concatenation along a channel dimension of the phase-specific feature maps 304_1-304_n. The information processing device 102 may concatenate n phase-specific feature maps 304 along the channel dimension C in the same chronological order as the phases are acquired (e.g. unenhanced features, arterial features, portal venous features—in that order—for the focal liver lesion detection example illustrated in FIGS. 2A and 2B). The number of channels in the resulting unified feature map 305 will remain C in this case, while the dimensionality in each channel will be multiplied by n, where n is the number of phases. This operation allows encoding of a dynamic enhancement pattern of the lesion in each channel of the unified feature map 305, while preserving phase-wise semantic information within each channel.

An example pseudocode for concatenating n phase-specific feature maps 304 ($P_1, \ldots, P_n$), each with width (W), height (H) and number of channels (C) is provided below.

```
1.  generate empty unified feature map (U) with width (n × W), height
    (H) and number of channels (C).
2.  for channel c in [1, C]:
        for phase-specific feature map P_i with i in [1, n]:
            for each location (x, y) in [1, W], [1, H] respectively:
                U[(i − 1)*W + x, y, c] = P_i[x, y, c]
```

Figure 5B:
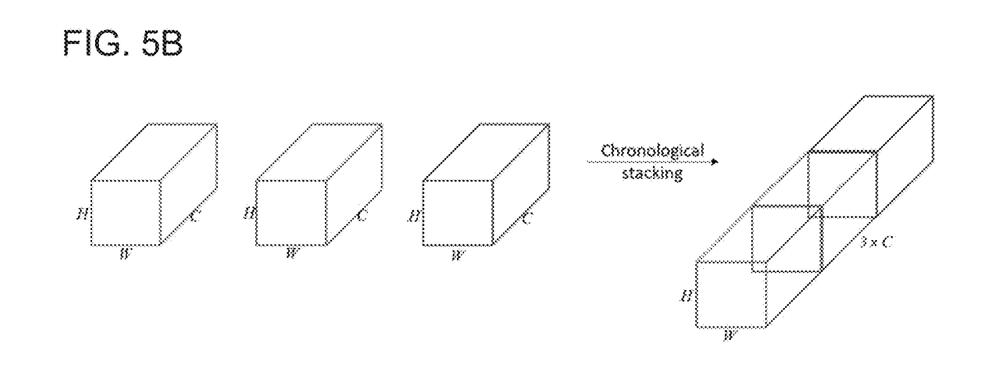
FIG. 5B illustrates another example method for performing feature fusion of feature maps, according to example embodiments.

FIG. 5B illustrates another example method for performing feature fusion of feature maps, according to example embodiments.

Referring to FIG. 5B, the information processing device 102 may combine (fuse) the phase-specific feature maps 304 to the unified feature map 305 via a chronological stacking across a channel dimension of the phase-specific feature maps 304. The information processing device 102 may stack n phase-wise feature maps 304 across channels chronologically, such that the number of channels in the resulting unified feature map is n×C, where C is the number of output channels as described above. The dimensionality in each channel remains the same as before the fusion. This operation encodes dynamic enhancement patterns of a lesion across the channels of the unified feature map 305, while preserving phase-wise semantic information within each channel.

An example pseudocode for stacking n phase-specific feature maps ($P_1, \ldots, P_n$), each with width (W), height (H) and number of channels (C) is provided below.

```
1.  generate empty unified feature map (U) with width (W), height (H)
    and number of channels (n × C).
2.  for phase-specific feature map P_i with i in [1, n]:
        for channel c in [1, C]:
            for each location (x, y) in [1, W], [1, H] respectively:
                U[x, y, (i − 1)*C + c] = P_i[x, y, c]
```

Phase-specific feature maps may be stored at specific locations along a channel (fusion via concatenation as shown in FIG. 5A) or within specific channels (fusion via stacking and shown in FIG. 5B) on the unified feature maps 305. Therefore, the detection and characterization heads 306 and 307 can leverage this structure to encode the chronological enhancement pattern of lesions.

Figure 5C:
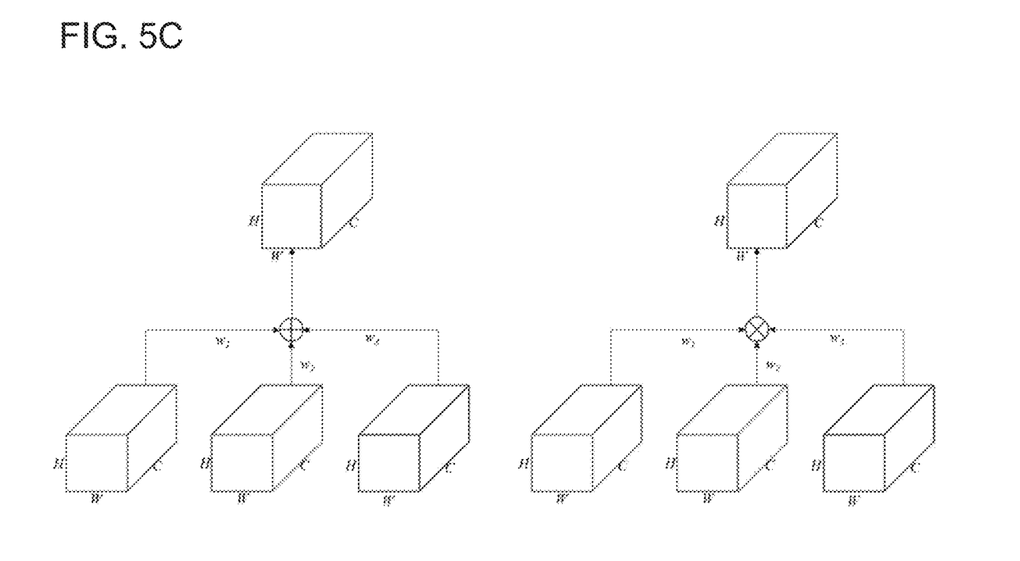
FIG. 5C illustrates another example method for performing feature fusion of feature maps, according to example embodiments.

FIG. 5C illustrates another example method for performing feature fusion of feature maps, according to example embodiments.

Referring to FIG. 5C, the information processing device 102 may combine (fuse) the feature maps to a unified feature map via a linear combination. The information processing device 102 may combine n phase-wise feature maps using linear algebraic mathematical operations. FIG. 5C illustrates examples of element-wise addition and element-wise multiplication. However, example embodiments are not limited thereto and any linear algebraic mathematical operations may be used.

According to example embodiments, the mathematical operations may be performed with or without phase-wise weights. Phase-wise weights can be scalar values that are multiplied to every element in the phase-wise feature map 304_1-304_n before the linear combination is carried out. These scalar values can be constants determined using domain knowledge (e.g., the portal venous phase is most promising for lesion detection in CE-CT exams, therefore a high weight may be applied to the corresponding feature map), and/or learned during the training phase along with other network parameters, etc. Phase-wise weights may also be anatomically guided and presented as a mask with the same dimensionality as the phase-wise feature map. In this case, element wise multiplication between the weight-mask and the phase-wise feature map would be performed before the linear combination is carried out. For example, a scalar weight may be applied to phase-wise feature maps by performing scalar multiplication of each element of the feature map with a single number.

An example pseudocode to obtain a linear combination of n phase-specific feature maps ($P_1, \ldots, P_n$), each with width (W), height (H) and number of channels (C), where f( . . . ) is a linear combination function with or without weights, such as element-wise addition or multiplication, is provided below.

```
1.  generate empty unified feature map (U) with width (W), height (H)
    and number of channels (C).
2.  for channel c in [1, C]:
        for each location (x, y) in [1, W], [1, H] respectively:
            U[x, y, c] = f(P_1[x, y, c], P_2[x, y, c], . . . , P_n[x, y, c])
```

The unified feature map 305, generated by linear combination has the same number of channels and dimensionality as any individual phase-wise feature map. Combining the individual phase-wise feature maps 304_1-304_n via linear combination may encode the dynamic enhancement pattern as localized peaks within higher-level semantic information across individual phase-wise feature maps.

The unified feature map 305 generated via linear combination may not always maintain the chronological information (e.g. commutative linear operations such as addition/multiplication). Therefore unified feature maps 305 generated via linear combination using commutative linear operations may be used for tasks where the chronological information is irrelevant (e.g., using multiple images from different phases "adds" more certainty for lesion detection). However, a more general non-commutative linear combination may be used for feature fusion, if required, to improve characterization performance.

As described above, FIGS. 5A-5C illustrate three example methods for combining (fusing) the phase-wise feature maps 304_1-304_n to the unified feature map 305. However, example embodiments are not limited thereto, and any known method for combining feature maps to a unified feature map while preserving a chronological order of the feature maps may be employed. Further, it should be understood that the fusion operation may be followed by another set of convolutional or fully connected layers for adaptive feature fusion.

Figure 6A:
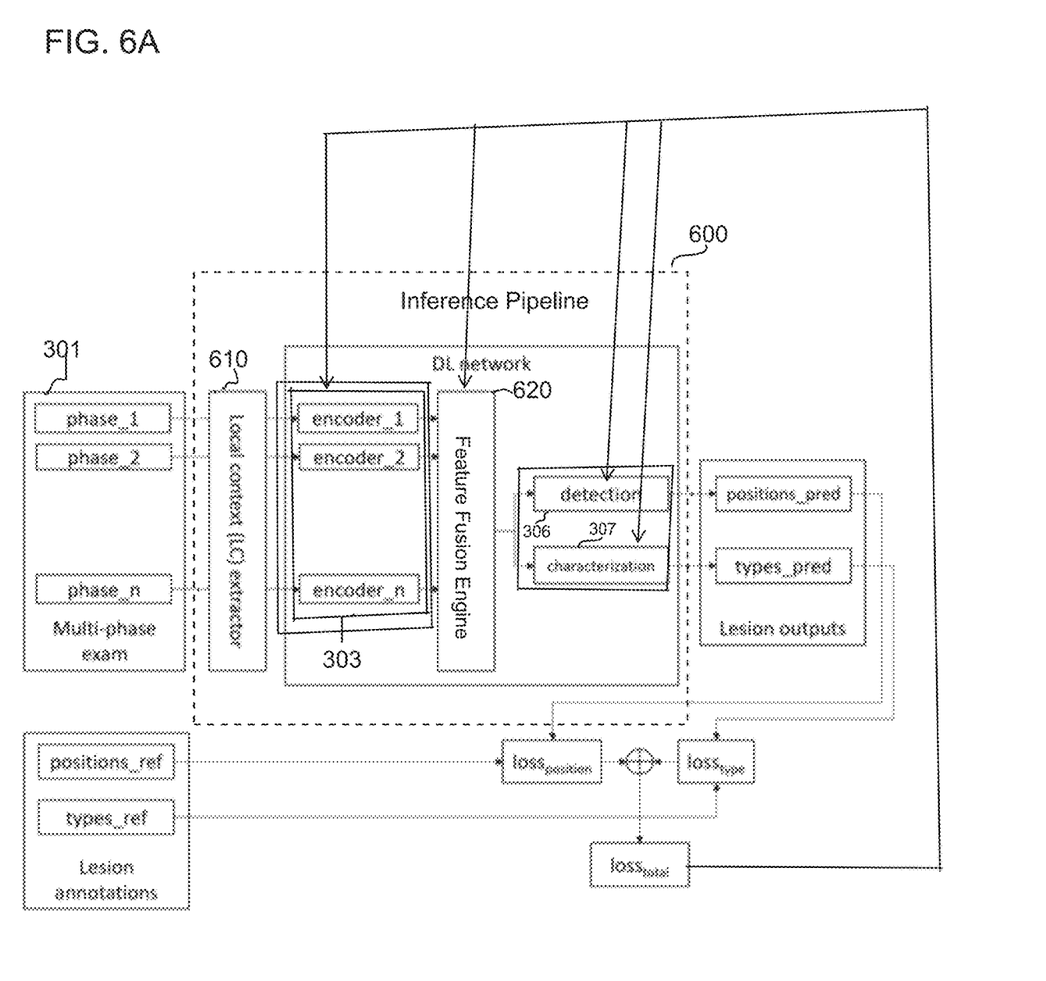
FIG. 6A illustrates a method according to example embodiments.

FIG. 6A illustrates a method according to example embodiments.

Referring to FIG. 6A, the information processing device 102 may train the encoders 303, the feature fusion engine 620, the detection heads 306, and/or the characterization heads 307 via an end-to-end training pipeline.

As shown in FIG. 6A, the information processing device 102 receives a set of multi-phase images 301. Reception of the multi-phase images 301 may be similar to step S301, described above.

The information processing device 102 determines positions and/or types of lesions based on the multi-phase images 301 using an inference pipeline 600. The inference pipeline 600 may include local context extractors 610, encoders 303, feature fusion engine 620, detections heads 306, and/or characterization heads 307. Operations performed by the inference pipeline 600 may be substantially similar to steps S302 to S305, described above. Repeated description is therefore omitted.

Returning to FIG. 6A, the processing device 102 compares predicted positions position_pred of lesions and predicted characterizations types_pred of lesions with position references positions_ref of the lesions and characterization references type_ref of the lesions, respectively, to determine a $loss_{position}$ and a $loss_{type}$.

As shown in FIG. 6A, the detection heads 306 output predicted positions position_pred, and the characterization heads 307 output characterization predictions types_pred. The processing device 102 compares the predicted positions positions_pred with position references positions_ref to compute a position loss $loss_{position}$. The information processing device 102 compares the characterization predictions types_pred with characterization references types_ref to compute a characterization loss $loss_{type}$. For example, the information processing device 102 may determine the position loss $loss_{position}$ and the characterization loss $loss_{type}$ using a mean squared error (MSE) function, a sum of squared errors (SSE) function, or any known function for computing loss.

The position reference positions_ref and characterization reference types_ref may be acquired from annotations performed by a medical professional. For example, a medical professional (e.g., an expert) may review phase images as prescribed by a clinical workflow and annotate the lesion positions as bounding boxes or in-painted masks. The lesion types may be separated by using different colors to annotate different lesion types. The annotations may be exported out of the clinical setting using structured reporting formats (e.g., DICOM RTSTRUCT).

The information processing device 102 computes a $loss_{total}$ based on the $loss_{position}$ and the $loss_{type}$. For example, the information processing device 102 may compute the $loss_{total}$ via element-wise addition of the $loss_{position}$ and the $loss_{type}$, as illustrated in FIG. 6A. However, example embodiments are not limited thereto and any element-wise algebraic mathematical operations may be used. Alternatively, the position and characterization losses $loss_{position}$ and $loss_{type}$ may be scalars. In this case, the information processing device may compute the $loss_{total}$ via algebraic operations.

The information processing device 102 determines whether the $loss_{total}$ is below a threshold. If the $loss_{total}$ is not below the threshold, then the information processing device 102 performs a backpropagation pass of all, or one or more, of the encoders 303, the feature fusion engine 620, the detection heads 306, and/or the characterization heads 307. For example, the information processing device 102 may update weights of the encoders 303, the feature fusion engine 620, the detection heads 306, and/or the characterization heads 307. The information processing device 102 may determine the weights for updating the encoders 303, the feature fusion engine 620, the detection heads 306, and/or the characterization heads 307 according to any known method.

If the $loss_{total}$ is below the threshold, then the information processing device 102 determines that the encoders 303, the feature fusion engine 620, the detection heads 306, and/or the characterization heads 307 are fully trained, and the training is complete.

Once the training is complete, a multi-phase exam including multi-phase images 301 may be passed to the inference pipeline 600 to localize and/or classify lesions.

Figure 6B:
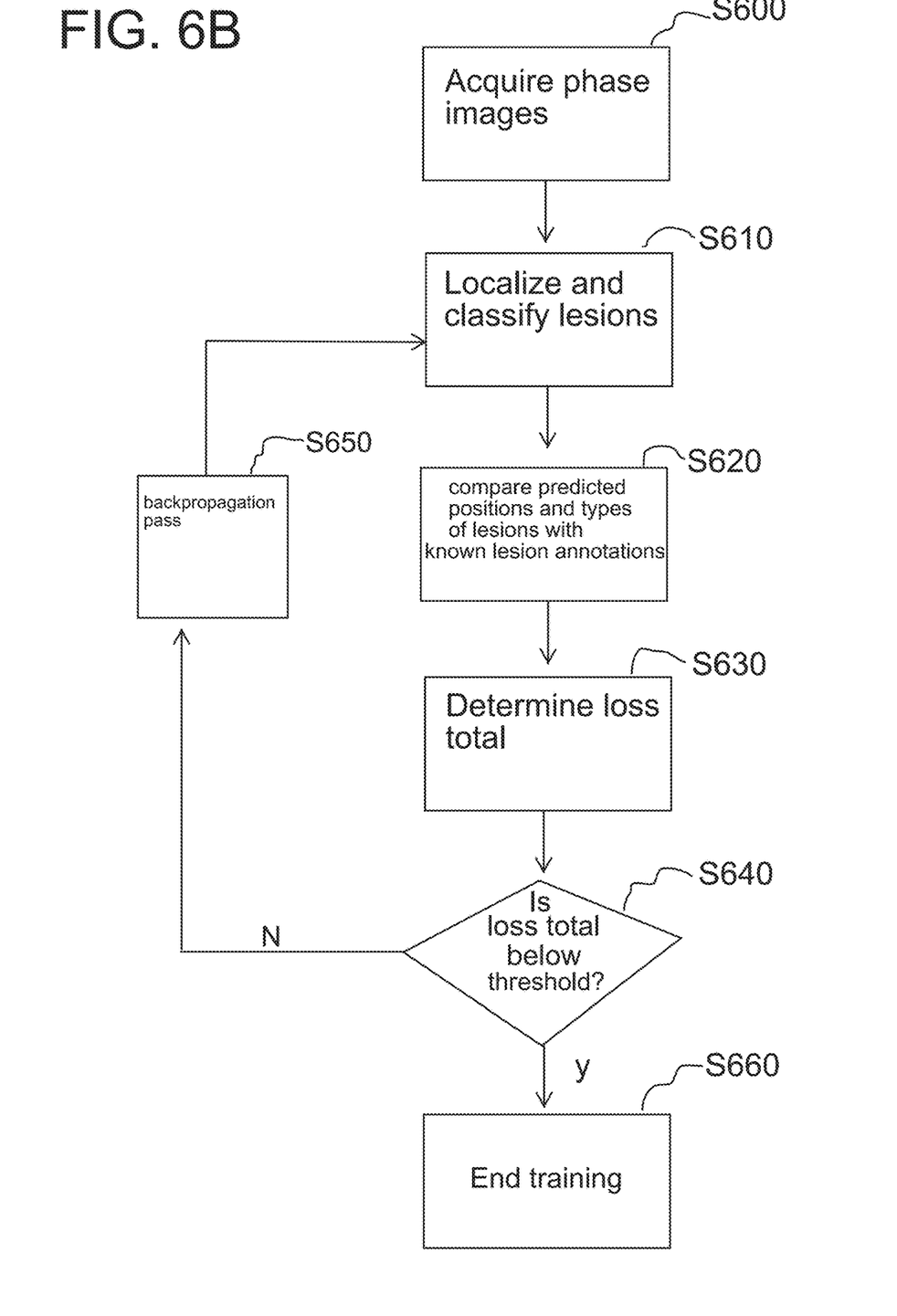
FIG. 6B is a flowchart illustrating a method according to example embodiments.

FIG. 6B is a flow chart illustrating a method according to example embodiments.

The operations shown in FIG. 6B may be similar to those described with reference to FIG. 6A. Repeated description has been omitted for brevity.

Referring to FIG. 6B, at step S600 the information processing device 102 receives a set of multi-phase images 301.

At step S610, the information processing device 102 localizes and classifies lesions in the multi-phase images 301 via the inference pipeline 600.

At step S620, the information processing device 102 compares the predicted positions position_pred of lesions and the predicted characterizations types_pred of lesions with position the references positions_ref of the lesions and the characterization references type_ref of the lesions, respectively, to determine the $loss_{position}$ and the $loss_{type}$.

At step S630, the information processing device 102 computes the $loss_{total}$ based on the $loss_{position}$ and the $loss_{type}$.

At step S640, the information processing device 102 determines whether the $loss_{total}$ is below a threshold. If the $loss_{total}$ is not below the threshold (N at step S640), then the information processing device 102 continues to step S650.

At step S650, the information processing device 102 performs a backpropagation pass of all, or one or more, of the encoders 303, the feature fusion engine 620, the detection heads 306, and/or the characterization heads 307. The information processing device 102 then proceeds to step S610 and repeats steps S610 to S640.

Returning to step S640, If the $loss_{total}$ is below the threshold (Y at step S640), then the information processing device 102 determines that the encoders 303, the feature fusion engine 620, the detection heads 306, and/or the characterization heads 307 are fully trained, and proceeds to step S660.

At step S660, the information processing device 102 determines that the training is complete, and ends the training.

Although the present invention has been described in detail with reference to example embodiments, the present invention is not limited by the disclosed examples from which the skilled person is able to derive other variations without departing from the scope of the invention.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific structural and functional details disclosed herein are merely representative for purposes of describing example embodiments. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, at least one central processing unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

What is claimed is:

1. A method for detection and characterization of lesions, the method comprising:
   acquiring a plurality of phase images of a multi-phase imaging exam;
   extracting a local context for each phase image of the plurality of phase images;
   encoding the local contexts to create phase-specific feature maps;
   combining the phase-specific feature maps chronologically to create a unified feature map; and
   at least one of characterizing or detecting a lesion based on the unified feature maps.

2. The method of claim 1, wherein the combining the phase-specific feature maps comprises concatenating the phase-specific feature maps along a channel dimension of the phase-specific feature maps.

3. The method of claim 1, wherein the combining the phase-specific feature maps comprises stacking the phase-specific feature maps chronologically across a channel dimension of the phase-specific feature maps.

4. The method of claim 1, wherein the combining the phase-specific feature maps comprises linearly combining the phase-specific feature maps.

5. The method of claim 4, wherein the linearly combining the phase-specific feature maps comprises combining the phase-specific feature maps using phase-wise weights.

6. The method of claim 1, wherein the extracting the local context comprises segmenting the plurality of phase images based on a mask of an organ of interest.

7. The method of claim 1, wherein the extracting the local context comprises sequentially extracting sub-images from the plurality of phase images.

8. The method of claim 1, wherein the encoding the local contexts comprises encoding the phase-specific feature maps using a convolutional neural network architecture.

9. The method of claim 8, wherein the convolutional neural network architecture is trained via an end-to-end training pipeline.

10. A device for detecting and characterizing lesions, the device comprising:
    a memory; and
    processing circuitry configured to cause the device to
        acquire a plurality of phase images of a multi-phase imaging exam,
        extract a local context for each phase image of the plurality of phase images,
        encode the local contexts to create phase-specific feature maps,
        combine the phase-specific feature maps chronologically to create a unified feature map, and
        at least one of characterize or detect a lesion based on the unified feature maps.

11. The device of claim 10, wherein the processing circuitry is further configured to cause the device to combine the phase-specific feature maps by concatenating the phase-specific feature maps along a channel dimension of the phase-specific feature maps.

12. The device of claim 10, wherein the processing circuitry is further configured to cause the device to combine the phase-specific feature maps by stacking the phase-specific feature maps chronologically across a channel dimension of the phase-specific feature maps.

13. The device of claim 10, wherein the processing circuitry is further configured to cause the device to combine the phase-specific feature maps by linearly combining the phase-specific feature maps.

14. The device of claim 13, wherein the processing circuitry is further configured to cause the device to linearly combine the phase-specific feature maps using phase-wise weights.

15. A non-transitory computer readable storage medium storing computer executable instructions that, when executed, cause an information processing device to perform a method for detecting and characterizing lesions, the method comprising:
    acquiring a plurality of phase images of a multi-phase imaging exam;
    extracting a local context for each phase image of the plurality of phase images;
    encoding the local contexts to create phase-specific feature maps;
    combining the phase-specific feature maps chronologically to create a unified feature map; and
    at least one of characterizing or detecting a lesion based on the unified feature maps.

16. The non-transitory computer readable storage medium of claim 15, wherein the combining the phase-specific feature maps comprises concatenating the phase-specific feature maps along a channel dimension of the phase-specific feature maps.

17. The non-transitory computer readable storage medium of claim 15, wherein the combining the phase-specific feature maps comprises stacking the phase-specific feature maps chronologically across a channel dimension of the phase-specific feature maps.

18. The non-transitory computer readable storage medium of claim 15, wherein the combining the phase-specific feature maps comprises linearly combining the phase-specific feature maps.

* * * * *